United States Patent [19]
Genieser et al.

[11] Patent Number: 5,625,056
[45] Date of Patent: Apr. 29, 1997

[54] DERIVATIVES OF CYCLIC GUANOSINE-3', 5'-MONOPHOSPHOROTHIOATE

[75] Inventors: Hans-Gottfried Genieser, Lemwerder-Ochtum; Ulrich Walter, Veitshöchheim; Elke Butt, Heissenbüttel, all of Germany

[73] Assignee: BIOLOG Life Science Institute, Germany

[21] Appl. No.: 511,664

[22] Filed: Aug. 7, 1995

Related U.S. Application Data

[63] Continuation-in-part of Ser. No. 430,164, Apr. 27, 1995, abandoned, which is a continuation of Ser. No. 64,555, May 21, 1993, abandoned.

[30] Foreign Application Priority Data

May 26, 1992 [DE] Germany ............... 42 17 679.4

[51] Int. Cl.$^6$ ............................................. C07H 19/213
[52] U.S. Cl. ................................................. 536/26.12
[58] Field of Search ........................... 536/26.12; 514/48

[56] References Cited

U.S. PATENT DOCUMENTS

| | | | |
|---|---|---|---|
| 3,872,082 | 3/1975 | Bergmeyer et al. | 536/26.12 |
| 3,883,508 | 5/1975 | Cook | 536/26.12 |
| 3,968,101 | 7/1976 | Christensen et al. | 536/26.12 |
| 4,728,730 | 3/1988 | Frey et al. | 536/26.12 |
| 4,797,480 | 1/1989 | Sorbi et al. | 536/26.12 |

FOREIGN PATENT DOCUMENTS

| | | | |
|---|---|---|---|
| 3802865 | 8/1989 | Germany | 536/26.12 |
| 8907108 | 8/1989 | WIPO | 536/26.12 |
| WO89/07108 | 8/1989 | WIPO | 536/26.12 |

OTHER PUBLICATIONS

Chem. Abstr., vol. 113, (1990) 111412 g.
Tetrahedron Letters, vol. 29, No. 23, (1988), pp. 2803–2804.
Advances in Second Messenger and Phosphoprotein Research, vol. 21, S. 83–86, (1988), Raven Press, New York.
Advances in Second Messenger and Phosphoprotein Research, vol. 25, S. 45–53 (1992), Raven Press, New York.
Barrio et al., "lin–Benzoadenine Nucleotides. Inter– and Intramolecular Interactions in Aqueous Solutions as Observed by Proton Magnetic Resonance," *J. Am. Chem. Soc.*, 101(6), 1564–1569 (1979).
Butt et al., "Inhibition of cGMP–Dependent Protein Kinase by (Rp)–guanosine 3',5'–monophosphorothioates," *FEBS Letters*, 26 3(1), 47–50 (1990); *Chem. Abstr.*, 113(13), p. 311,Abstr. No. 11412g (1990).
Sandberg et al., "Characterization of Sp–5,6–dichloro–1–β–D–ribofuranosyl–benimidazolo–3', 5'–Monophosphorothioate (Sp–5,6–DCl–cBiMPS) as a Potent and Specific Activator of Cyclic–AMP–Dependent Protein Kinase in Cell Extracts and Intact Cells," *Biochem. J.*, 279, 521–527 (1991).

Nass et al., "Mapping of the Epitope/Paratope Interactions of a Monoclonal Antibody Directed Against Adenosine 3',5'–monophosphate," *Biochem. J.*, 285, 129–136 (1992).

Meijer et al., "Starfish Oocyte Maturation: Evidence for a Cyclic AMP–Dependent Inhibitory Pathway," *Developmental Biol.*, 133, 58–66 (1989).

Eckstein et al., "Stereochemical Course of the Reaction Catalyzed by the Cyclic GMP Phosphodiesterase from Retinal Rod Outer Segments," *J. Biol. Chem.*, 263(28), 14080–14085 (1988).

Ouedraogo et al., "Effects of Cyclic AMP and Analogues on Neurogenic Transmission in the Rat Tail Artery," *J. Pharmacology*, 111, 625–631 (1994).

Chao et al., "Activation of Intestinal CFTR Cl– Channel Enterotoxin and Guanylin via cAMP–Dependent Kinase," *EMBO Journal*, 13(5), 1065–1072 (1994).

Moretto et al., "Nitric Oxide Regulates Luteinizing Hormone–Releasing Hormone Secretion," *Endocrinology*, 133(5), 2399–2402 (1993).

(List continued on next page.)

*Primary Examiner*—John Kight
*Assistant Examiner*—L. Eric Crane
*Attorney, Agent, or Firm*—Nixon & Vanderhye

[57] ABSTRACT

New derivatives of $S_P$- and $R_P$-configures cyclic guanosine-3',5'-phosphorothioates and their physiologically and pharmaceutically acceptable salts according to the general formula

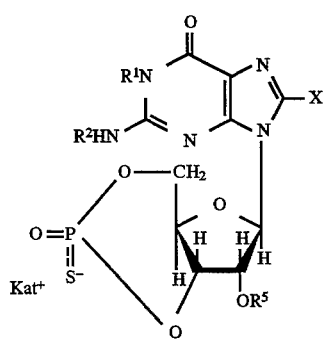

are cell membrane permeable inhibitors ($R_P$-isomers) and stimulators ($S_P$-isomers) of cyclic GMP-dependent protein kinase which are resistant against phosphodiesterase degradation and suitable as ligands for affinity chromatography of cyclic nucleotide-dependent binding proteins.

17 Claims, No Drawings

OTHER PUBLICATIONS

Flaadt et al., "Cyclic AMP– and Ins(1,4,5)P$_3$–Induced Ca$^{2+}$ Fluxes in Permeablised Cells of *Dictyostelium*: cGMP Regulates Ca$^{2+}$ Entry Across the Plasma Membrane," *J. Cell Science*, 105, 255–261 (1993); incomplete copy submitted—completed copy supplied by PTO.

Klyszcy–Nasko et al., "Modulation of Bradykinin–Induced Calcium Signals by Oxidative Stress in PC12 Cells," *Arch. Biochem. Biophys.*, 306(2), 383–390 (1993).

Genieser et al., "Synthesis of Nucleoside–3',5'–Cyclic Phosphorothioates by Cyclothiophosphorylation of Unprotected Nucleosides," *Tetrahedron Letters*, 29(23), 2803–2804 (1988).

Corbin et al., "Mechanism and Function of cAMP– and cGMP–Dependent Protein Kinases," in vol. 21 of *Adv. in Second Messenger and Phosphoprotein Research*, Adelstein et al. (eds.), Raven Press, New York, NY, 1988, pp. 75–86, see particularly pp. 83–86.

Thomas et al., "Partial Mapping of Cyclic Nucleotide Sites and Studies of Regulatory Mechanisms of Phosphodiesterases Using Cyclic Nucleotide Analogues," in vol. 25 of *Adv. in Second Messenger and Phosphoprotein Research*, Raven Press, New York, NY, 1992, pp. 45–53.

DERIVATIVES OF CYCLIC GUANOSINE-3', 5'-MONOPHOSPHOROTHIOATE

This application is a continuation-in-part of application of Ser. No. 08/430,164, filed Apr. 27, 1995, now abandoned, which is a continuation of Ser. No. 08/064,555, filed May 21, 1993, now abandoned.

FIELD OF THE INVENTION

The present invention relates to new derivatives of $S_P$- and $R_P$-configurated cyclic guanosine-3',5'-phosphorothioate derivatives and their physiologically acceptable salts.

BACKGROUND AND BRIEF DESCRIPTION OF THE INVENTION

Since its discovery by Sutherland (Ann. Rev. Biochem., 37, 149 (1968)) the central role of cyclic adenosine-3',5'-monophosphate (cAMP) as a cellular signal transduction molecule (second messenger) has been validated in numerous biochemical processes.

The corresponding guanosine-3',5'-monophosphate (cGMP) obviously controls also quite a lot of cellular biological functions, e. g. the relaxation of contracted muscle of the aorta or the inhibition of thrombocyte function (Walter, U., Rev. Physiol. Biochem. Pharmacol., 113, 42–88 (1989)).

cGMP can either support the cAMP signal pathway or can stimulate a contrary effect as a regulatory opponent.

Normally, cAMP and cGMP are formed by intracellular cyclases from ATP and GTP, respectively, after external stimulation by a hormone. During the signal transduction process both compounds bind to specific protein kinases which in turn can activate or deactivate target proteins by phosphorylation.

Up to now several different cyclic nucleotide-dependent phosphodiesterases are known which metabolize cAMP and cGMP (Beavo, J. A., Second Messenger and Phosphoprotein Res., 22, 1–38 (1988)) and which are responsible for switching off a given signal.

Since several cellular functions are connected with unnaturally elevated or depressed low levels of cAMP oder cGMP, there is considerable interest in basic research on corresponding second messenger systems mainly on the level of suitable modeling cell culture experiments.

In cultured cells intracellular levels of cAMP or cGMP which are too low, for example, can be compensated by specific inhibitors of cyclic nucleotide-dependent phosphodiesterases (Nicholson et al., TIBS 12, 19–27 (1991)) preventing metabolic degradation and resulting in cyclic nucleotide accumulation.

In addition, application of membrane permeable chemical modifications of cAMP and cGMP such as 8-bromo-cAMP/cGMP or 8-(4-chlorophenyl-thio)-cAMP/cGMP can directly activate the corresponding protein kinases in order to compensate low cyclic nucleotide levels. Chemically modified cyclic nucleotides can also be used for the in vitro characterization of kinase specificity (Wolfe et al. J. Biol. Chem., 264, 7734–7741 (1989), Geiger et al., Proc. Natl. Acad. Sci. USA, 89, 1031–1035 (1992)).

Finally, use of cyclase stimulators forskolin, cholera toxin, nitroprussid, NO) results in higher production rates of the corresponding second messenger, i.e. the intracellular concentration of cAMP and cGMP can be increased.

On the other hand, a potential decrease or even a complete inhibition of the cAMP or cGMP signal pathway is of predominent importance as well.

Presently, some isoquinoline derivatives (Chijawa et al., J. Biol. Chem., 265, 5267 (1990)) and a protein-based structure (Walsh et al., J. Biol. Chem., 246, 1977, (1971)), are used as inhibitors of cyclic nucleotide-dependent protein kinases. In addition, $R_P$-configurated derivatives of adenosine-3',5'-monophosphorothioate ($R_P$-cAMPS) have been used for inhibition of cAMP-mediated biological effects.

$R_P$-cAMPS is an antagonist of cAMP and a competitive inhibitor of cAMP-dependent protein kinases type I and II (cAK I & II) (Botelho et al., Methods Enzymol., 159, 159 (1988)). Other diastereomeric cAMPS derivatives with $R_P$-configuration were already synthesized (Dostmann et al., J. Biol. Chem., 265, 10484 (1990)). Their biological properties are presently tested.

With respect to cAMPS derivatives it has been found that not all $R_P$-configurated diastereomers necessarily must be inhibitors of cAK but also can have agonistic effects (Sandberg et al., Biochem. J., 279, 521–527 (1991)). Most of the about 20 $R_P$-isomers tested so far are only partial antagonists or rather agonists of cAK and up to now there is no structural criterion which allows a reliable prediction whether or not a certain $R_P$-configurated adenosine-3',5'-monophosphorothioate derivative can completely block cAK I or cAK II, respectively.

In contrast to cAMPS derivatives only two sulfur-modified compounds of cGMP with inhibitory properties have been described: $R_P$-Guanosine-3',5'-monophosphorothioate ($R_P$-cGMPS) and $R_P$-8-chloroguanosine-3',5'-monophosphorothioate ($R_P$-8-Cl-cGMPS) (Butt et al., FEBS Lett., 263, 47 (1990)).

However, a potential use of these compounds as inhibitors of the cGMP signal pathway is opposed by severe drawbacks. Particularly, $R_P$-cGMPS lacks the required specificity for cGMP-dependent protein kinase (cGK) and inhibits cAK as well. In addition, the required lipophilicity which is important for cell membrane penetration properties is rather poor for both compounds, although hydrophobicity in average is doubled by modification with sulfur (Braumann et al., J. Chromatogr., 350, 105–118 (1985)).

Therefore, the object of the invention is to find new derivatives of cGMP which exhibit considerably higher lipophilicity and cell membrane permeability and which can inhibit cGK competitively and selectively. In addition such compounds should have sufficient chemical, physical and metabolical stability which would enable their use as stable ligands for affinity chromatography.

DESCRIPTION OF THE PREFERRED EMBODIMENTS

This object is solved by the compounds of claim 1.

Surprisingly it has been found that the above of advantegeous inhibitors of cGMP-depending protein kinase are met by the $R_P$-configurated cGMPS derivatives according to the invention.

It was particularly surprising that even modifications which obviously can partially stimulate cAMP-dependent protein kinase in form of their corresponding $R_P$-cAMPS derivatives are definitly inhibitors of cGMP-depending protein kinase in case of $R_P$-cGMPS analoges. Furthermore, the high selectivity and the stability of the claimed compounds towards phosphodiesterases is especially advantgeous. Inhibiting or activating effects on corresponding cAKs are noticed only at concentrations much higher than those which have to be applied in case of cGK. The $S_P$-configurated cGMPS derivatives according to the invention are suitable as metabolically stable cGK activators (activators of cGMP-dependent protein kinases).

The compounds of the present invention exhibit several properties which allow their intensive use in basic cellular signal transduction research, e.g. as modulators of cGMP-regulated processes, either as inhibitors ($R_P$ configuration) or as activators ($S_P$ configuration). In addition, the claimed compounds are useful as metabolically stable ligands for affinity chromatography of cGMP-binding proteins such as protein kinases and phosphodiesterases. Here, the claimed phosphorothioate derivatives allow very mild conditions for desorption of the absorbed protein from the column, but exhibit enough specifity and affinity for cGMP binding sites.

As already known, the modification with sulfur ensures total stability towards cyclic nucleotide-dependent phosphodiesterases of mammalian origin including man in case of all $R_P$-configurated compounds. For the corresponding derivatives with $S_P$-configuration the sulfur modification leads to considerable retardation or to total resistance against enzymatic degradation by cyclic nucleotide phosphodiesterases.

This metabolic stability is a further advantage for their special utility as affinity chromatography media. It prolongs the life time of the ligand and allows riskless purification of phosphodiesterases which normally very effectively cleave cyclic nucleotides.

In comparison to already known nucleotide cyclic phosphates the claimed compounds according to formula I have increased lipophilicity and hence better membrane permeability. Axial substitution of the phosphate moiety with sulfur ($S_P$-diastereomers) leads to cGK activating compounds, whereas an equatorial position of sulfur results in cGK antagonists ($R_P$-Diastereomers).

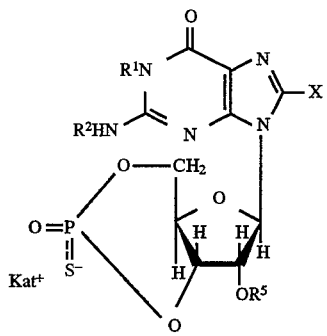

I

Both, $R^1$ and $R^2$ are hydrogen, while X is —$CF_3$ or a —$NR^3R^4$ or —$SR^4$ group, wherein $R^3$ is hydrogen and $R^4$ is an alkyl group with a terminal $NH_2$ or OH group, or is a phenyl group having in the 4-position a substituent Y and having the formula:

wherein

Y is —F, —Cl, —Br, —I, —OH, —SH, —$NH_2$, —$NO_2$, —$OCH_3$, —$CH_3$ or $CF_3$, or $R^3$ and $R^4$ both are alkyl groups which are connected to each other to form a ring, provided X is not a thiobenzyl group, or $R^1$ and $R^2$ together are a styrylene group and form a condensed tricyclic ring system according to formula II:

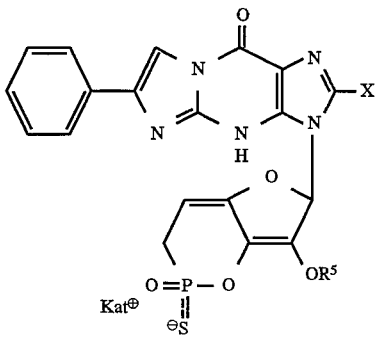

wherein $R^5$ is hydrogen, an alkylsilyl group or an acyl group, and $Kat^+$ is a proton or another physiologically acceptable metal cation or a trialkylammonium ion, X is hydrogen, —F, —Cl, —Br, —I, $CF_3$ or an —$NR^3R^4$, —$SR^4$ group, wherein $R^3$ is hydrogen and $R^4$ is an alkyl group with a terminal $NH_2$ or OH group.

In both cases compounds having hydrophobic aromatic substituents in position 8 are preferred since they show very high lipophilicity which enables their use even for intact cells. Especially preferred are compounds substituted in position 8 by phenylthio groups, e.g. 4-chlorophenylthio- or 4-hydroxyphenylthio groups.

Preferred as well are structures according to formula II which carry halogens in position 8 of the nucleobase.

In addition, especially those compounds are important which, without sulfur modification, are already established tools in biochemistry, such as 8-(4-chlorophenylthio) guanosine-3',5'-monophosphate (8-pCPT-cGMP) or β-phenyl-1,$N^2$-ethenoguanosine-3',5'-monophosphate (PET-cGMP) and their derivatives.

Preferred metal cations are Na+, K+, Li+, ½ $Ca^{2+}$ and ½ $Mg^{2+}$.

In order to further enhance the membrane permeability of the invented compounds it can be advantageously to modify the 2'-hydroxyl group of the pentose group with hydrophobic groups, which after penetration of the cellular membrane can be cleaved again, i.e. hydrolytically, by intracellular enzymes.

Suitable modifications for enzymatic cleavage of 2'-protecting groups include esters of linear or branched carboxylic acids of short or medium chain length ($C_1$–$C_8$). Especially preferred is the n-butyryl group.

An example for groups that can be cleaved hydrolytically from the 2'-hydroxyl group are silyl groups. Especially suitable are trialkylsilyl groups, in particular the trimethylsilyl groups having linear or branched $C_1$–$C_5$ alkyl substituents.

Due to their specific binding properties and their resistance against enzymatic hydrolysis the claimed compounds are suitable for preparing stationary phases for liquid chromatography, especially for affinity chromatography of cyclic nucleotide-dependent binding proteins. In this case the invented compounds are immobilized to insoluble polymeric carriers by means of reactive terminal groups like halogen, amino or hydroxyl groups. These reactive groups are coupled to the heterocyclic nucleobase either directly (e.g. X=halogen, —$NH_2$ or —OH) or by molecular spacers.

Preferred are spacers of the structure X=—$NHR^4$ or —$SR^4$, wherein $R^4$ is a linear alkyl group with a reactive terminal —$NH_2$ or —OH group. Especially preferred are spacers having a length of 2–12 atoms.

Suitable for the insoluble polymeric matrix are silica gels, glass, silicone polymers, polyacrylamide, polystyrene, agarose (e.g. Sepharose®), cellulose or dextrane (e.g. Sephadex®). Preferred materials comprise matrices which already contain spacers and which are suitable for immobilization of those of the claimed compounds which contain no spacers. This is true, for example, for ready-to-use materials which are commercially offered for immobilization of various affinity ligands, such as Fractogel TSK®, CNBr- or epoxy-activated agarose, dextrane or porous glass (CPG).

Synthesis of the new compounds is performed either by cyclothiophosphorylation of correspondingly modified nucleosides in trialkyl phosphates with $PSCl_3$ (Genieser et al., Tetrahedron Lett., 29, 2803 (1988); WO 89/07108; DE-OS 38 02 685), by nucleophilic substitution of halogen at preformed 8-halogenated cGMPS analogs with corresponding nucleophiles (Miller et al., Biochemistry 12, 5310–5319 (1973) or by modification of preformed cGMPS analogs with 2-bromoacetophenone (Miller et al., Biochem. Pharmacol., 30, 509–515 (1981)).

The derivatization of the 2'-hydroxyl group is performed by standard methods. For example, the 2'-hydroxyl group is conveniently esterified by means of carboxylic acid chlorides or anhydrides in presence of pyridine.

Silyl protecting groups are introduced by treating the phosphorothioates with trialkyl silyl chlorides and pyridine (Gaffney et al.; J. Am. Chem. Soc.; 104, 1316–1319 (1982)).

Immobilization of the claimed compounds to specially prepared ready-to-use carrier materials by hydrolysis resistant bonds follows already known procedures. Normally, the affinity ligand according to the invention is stirred at room temperature or at higher temperatures with the preactivated carrier material in buffered solution.

Lipophilicity determinations of the invented compounds are performed using reversed-phase-high pressure liquid chromatography as has already been described by Braumann et al., (J. Chromatogr., 350, 105–118 (1985)). The resulting log $K_W$ values are comparable to log P values and are a measure of lipophilicity. The polar parent compound cGMP has been reported to have a log $K_W$ of 0.85. Recent determinations gave a log $K_W$ of 0.77.

Isolation of cGK I from bovine lung and of cAK II from bovine heart is performed as has been already published (Walter et al., J. Biol. Chem., 255, 3757–3762 (1980)). Protein kinase activity is determined according to the method of Roskoski (Methods Enzymol., 99, 3–6 (1983)). In vitro data on membranes of human thrombocytes are obtained as has already been described by Halbrügge et al. (Eur. J. Biochem., 185, 41–50, (1989)).

cGK inhibitors dose-dependently inhibit the cGMP-modulated phosphorylation of a 46/50 kDa band but do not interfere with the cAMP-dependent phosphorylation of the 22 kDa- and 240 kDa band. Compounds with extraordinary good membrane permeability are tested in vivo with intact human thrombocytes according to Halbrügge et al. CJ. Biol. Chem., 265, 3088–3093 (1990)).

SPECIFIC EXAMPLES

EXAMPLE 1

Cyclic 8-(4-chlorophenylthio)-guanosine-3',5'-monophosphorothioate, $R_P$-/$S_P$-diastereomers ($R_P$-/$S_P$-8-pCPT-cGMPS)

Synthesis of these compounds is performed by nucleophilic substitution of $R_P$-8-Br/Cl-cGMPS with 4-chlorothiophenol as has already been described in principle by Miller et al., (Biochemistry 12, 5310–5319 (1973)) or by cyclothiophosphorylation of 8-(4-chlorophenylthio) guanosine according to Genieser et al. (Tetrahedron Lett., 29, 2803 (1988); WO 89/07108; DE-OS 38 02 685).

Briefly, $R_P$-8-Br/Cl-cGMPS, triethyl ammonium salts, are refluxed with excess 4-chlorothiophenol in methanol-containing aqueous solution until the starting nucleotide can no longer be detected by high pressure liquid chromatography (RP-18, 9% acetonitrile/25 mM of triethyl ammonium phosphate buffer). The raw product is purified by means of column liquid chromatography using a silica-based reversed phase (RP-18 material, 30% methanol, 100 mM triethyl ammonium formate buffer).

The product containing fractions are collected, lyophilized and repeatedly purified by the same chromatographic system, if necessary.

Yield: 62% (substitution) and 5% (cyclothiophosphorylation) respectively. The typical purity is higher than 98% while no traces of the kinase-stimulating $S_P$-isomer and less than 0.05% of 8-pCPT-cGMP are detectable.

Formula: $C_{16}H_{15}O_6N_5S_2PCl$ (MG: 503.9; freie Säure)
UV: ($H_2O$): $\lambda_{max}$=276 nm ($\epsilon$=21,500 bei pH 7).

| $R_P$-8-pCPT-cGMPS | $S_P$-8-pCPT-cGMPS |
|---|---|
| FAB-MS (Na-salt in glycerol): Negative mode | |
| m/z = 292 (10%: Base –H)⁻ | m/z = 292(10%: Base –H)⁻ |
| m/z = 502(55%: M – H)⁻ | m/z = 502(30%: M – H)⁻ |
| m/z = 594(35%: M – H + Gly)⁻ | m/z = 524(10%: M – H + Gly)⁻ |
| Positive mode | |
| m/z = 294(30%: B + H)⁺ | m/z = 504(1%: M + H)⁺ |
| m/z = 504(15%: M + H)⁺ | |
| m/z = 526(20%: M + Na)⁺ | |
| m/z = 548(20%: M + 2 Na)⁺ | |
| ¹H-NMR(DMSO-$d_6$/TMS): | |
| δ = 5.84 ppm (s: H1') | δ = 5.89 ppm (s: H1') |
| ³¹P-NMR (MeOH/$H_3PO_4$): | |
| δ = 58.4 ppm | δ = 56.5 ppm |
| Lipophilicity: | |
| Log $k_w$ = 2.82 | Log $k_w$ = 2.84 |

Biological Properties $R_P$-8-pCPT-cGMPS is a competitive inhibitor of isolated cGK I. Its inhibition constant $K_i$ is 0.7 µM.

At high concentrations the compound is a weakly partial agonist for cAK II with an activation constant $K_a$ of 400 µM.

$R_P$-8-pCPT-cGMPS inhibits the phosphorylation of a 46/50 kDa-band in membranes of human thrombocytes. In contrast, the cAMP-dependent phosphorylation of a 22- and a 240 kDa-band, respectively, is not disturbed. The compound shows excellent cell membrane permeability and inhibits the cGMP-dependent phosphorylation even in intact human thrombocytes.

In contrast, $S_P$-8-pCPT-cGMPS is an activator for both isolated cGK and cGMP-mediated phosphorylation in vivo.

Both compounds are not hydrolyzed by Ca/Calmodulin dependent phosphodiesterase.

$R_P$-8-pCPT-cGMPS is a poor inhibitor of the cGMP-inhibited phosphodieserases (cGI-PDE) and thus does not interfere with the regulation of the cAMP signal pathway.

EXAMPLE 2

Cyclic β-phenyl-1,$N^2$-ethenoguanosine-3',5'-monophosphorothioate, $R_P$-/$S_P$-diastereomers ($R_P$-/$S_P$-PET-cGMPS)

A.

231 mg (500 μmol) of cyclic $R_P$- (or $S_P$)-guanosine-3',5'-monophosphorothioate, triethylammonium salt, (BIOLOG, Bremen, FRG) are dissolved in 5 ml of dry dimethylsulfoxide. 100 μl of 1,8-Diazabicyclo-[5.4.0]-undec-7-ene and 100 mg of 2-bromoacetophenone are added and the mixture is stirred at room temperature. After 4 hours another 100 mg of 2-bromoacetophenone are added. The reaction is followed by high pressure liquid chromatography using a silica-based anion exchange column and 40% methanol/400 mM phosphate buffer. After dissappearence of the $R_P$-($S_P$)-cGMPS signal (approx. 24 h) the reaction is quenched by addition of 10 ml of water. The solution is adjusted to pH 7, filtered and adjusted to pH 1.5 by hydrochloric acid. The precipitate is washed with water and acetone subsequently. For further purification the product is dissolved in water by addition of sodium hydroxide, precipitated again by hydrochloric acid and finally washed with water and acetone respectively. Yield: 46 mg (12%). The purity is higher than 90%.

B.

Synthesis is performed as has already been principally described (Genieser et al., Tetrahedron Lett., 29, 2803 (1988); WO 89/07108; DE-OS 38 02 685).

Briefly, 383 mg (1 mmol) of PET-guanosine (BIOLOG, Bremen, FRG) are dissolved in 5 ml of triethyl phosphate. While gently stirring 203 μl (2 mmol) of thiophosphoryl chloride are added. The reaction is followed by high pressure liquid chromatography using a silica-based reversed phase column (RP-18, 50% methanol/100 mM of triethyl ammonium formate buffer). After disappearence of the starting nucleoside the solution is poured into a refluxing mixture containing 60% acetonitrile and 0.08M potassium hydroxide. After neutralization with hydrochloric acid the solution is cooled down and evaporated to dryness. The residue is purified by means of column liquid chromatography using a silica-based reversed phase material (RP-18, 30% methanol, 10 mM triethyl ammonium buffer) and yields the separated diastereomers $R_P$- and $S_P$-PET-cGMPS.

Subsequently, each isomer is further purified by applying the same chromatographic system. 70 μmol (7%) of $R_P$-PET-cGMPS are obtained as triethyl ammonium salt. Its typical purity is higher than 98% while no traces of the kinase-stimulating $S_P$-isomer and less than 0.05% of PET-cGMP are detectable. $S_P$-PET-cGMPS is obtained as triethylammonium salt in a yield of 41 μmol (4%). Its purity is higher than 98%.

Formula: $C_{16}H_{16}O_6N_5SP$ (MG: 461.4; freie Säure)
UV ($H_2O$): $\lambda_{max}$=252 nm (ε=37,400 at pH 7).

| $R_P$-PET-cGMPS | $S_P$-PET-cGMPS |
|---|---|
| FAB-MS (Na salts in glycerol): | |
| Negative mode | |
| m/z = 250(10%: Base −H)− | m/z = 250(70%: Base −H)− |
| m/z = 460(10%: M − H)− | m/z = 460(70%: M − H)− |
| m/z = 482(6%: M − 2 H + Na)− | m/z = 482(0.1%: M − 2 H + Na)− |
| Positive mode | |
| m/z = 252(40%: Base + H)+ | m/z = 252(15%: Base + Na)+ |
| m/z = 484(5%: M + H + Na)+ | m/z = 462(4%: M + H)+ |
| $^1$H-NMR(DMSO-$d_6$/TMS): | |
| δ = 6.01 ppm(s: H1') | δ = 5.99 ppm(s: H1') |
| $^-$P-NMR(MeOH/$H_3PO_4$): | |
| δ = 58.3 ppm | δ = 56.5 ppm |
| Lipophilicity | |
| Log $K_w$ = 2.81 | Log $K_w$ = 2.83 |

EXAMPLE 3

Cyclic β-phenyl-1,$N^2$-etheno-8-bromoguanosine-3',5'-monophosphorothioate, $R_P$/$S_P$-diastereomers ($R_P$-/$S_P$-8-Br-PET-cGMPS)

480 μmol of $R_P$-8-bromoguanosine-3',5'-monophosphorothioate (Biolog, Bremen) are dissolved in 40 ml of dimethylsulfoxide. 484 μl of 1,8-diazabicyclo-(5.4.0)-unde-7-ene in 6 ml of acetonitrile and 4.2 ml of a solution of 2-bromoacetophenone in acetonitrile are added and the mixture is stirred at room temperature. The decrease of the cyclic nucleotide is monitored by HPLC (RP-18,4% propanol-2, 20 mM triethylammonium formate buffer, 1.5 ml/min., UV 254 nm). After completion of the reaction the raw mixture is diluted with 160 ml of water and adjusted to pH 7 by hydrochloric acid. After the precipitate formed has been dissolved by addition of some propanol-2, the solution is applied on a weak anion exchange column (Fractogel TSK DEAE 650). At first elution with water is performed, then 40% propanol-2 with increasinfg NaCl content is pumped, starting with 30 mM. Finally, the product is eluted with 500 mM NaCl/40% propanol-2. Product-containing fractions are collected and evaporated to about 100 ml. The raw product is subsequently purified on a reversed phase silica column (RP-8) by elution with 80% methanol/water. Product containing fractions are collected and evaporated. $R_P$-/$S_P$-8-Br-PET-cGMPS is isolated with a purity of >98%, the yield is 21%.

Formula: $C_{18}H_{15}O_4N_5SPBr$ (MG: 540.3; free acid)
UV ($H_2O$): $\lambda_{max}$=256.5 nm (ε=39,400 at pH 7).

$R_P$-Br-PET-cGMPS

FAB-MS (Na salt in glycerol):
Negative mode
m/z=328/330 (30%: Base −H)−
m/z=460 (2%: M−Br−H)−
m/z=482 (4%: M−Br−H+Na)−
m/z=538/540 (2.5%: M−H)−
m/z=560/562 (4%: M−H+Na)−
Positive mode
m/z=484 (10%: M+H+Na−Br)+
m/z=562/564 (15%: M+H)+
$^{31}$P-NMR (MeOH/$H_3PO_4$):
δ=58.1 ppm
Lipophilicity
Log $K_W$=3.22

Biological Properties $R_P$-8-Br-PET-cGMPS is a competitive inhibitor of cGMP-dependent protein kinases, its inhibition constant is Ki 0.03 μM.

$R_P$-8-Br-PET-cGMPS blocks selectively the cGMP signal transduction pathway without affecting cAMP-mediated effects.

For example, the SIN 1-stimulated relaxation in perfused aorta muscle and cGMP-dependent phosphorylation of three proteins of the masses 46, 50 and 130 kDa is inhibited.

The effectivity of this inhibitor at thrombocyte membranes surpasses $R_P$-8-pCPT-cGMPS by a factor of 5–10.

EXAMPLE 4

Immobilization of a $R_P$-cGMPS Analog to a Gel with Preformed Spacer 200 ml of Fractogel TSK AF Amino 650® (E. Merck, Darmstadt, FRG) are washed in order to remove stabilizers and are subsequently suspended in 100 ml sodium acetate buffer. 280 mg (500 µmol) $R_P$-8-Br-cGMPS, triethylammonium salt, are added and the mixture is gently stirred at 80° C. The decrease of the free phosphorothioate is monitored by high pressure liquid chromatography (RP-18, 10% methanol, 100 mM triethylammonium formate buffer). After completion of the reaction the suspension is filtered and washed until changes in UV absorbtion at 260 nm can no longer be observed in the filtrate. The material is stored in water containing 1 mM sodium azide in order to prevent microbial growth.

EXAMPLE 5

Cyclic 8-(2-aminoethyl)aminoguanosine-3',5'-monophosphorothioate, $R_P$-/$S_P$-diastereomers ($R_P$-/$S_P$-8-AEA-cGMPS)

541 mg (1 mmol) of $S_P$-8-Br-cGMPS, triethyl ammonium salt, are dissolved in 30 ml of water. 30 ml of diaminoethane are added and the mixture is refluxed until no starting nucleotide is left.

The reaction is followed by high pressure liquid chromatography (RP-18, 4% methanol, 10 mM triethyl ammonium formate buffer). After completion the mixture is evaporated to dryness, and repeatedly evaporated with methanol.

$S_P$-8-AEA-cGMPS is obtained with 97% purity, the yield is determined by UV to be 909 µmol (91%). The corresponding $R_P$-isomer is synthesized likewise.

Formula: $C_{12}H_{18}O_6N_7SP$ (MW 419.4 (free acid)
UV: ($H_2O$): $\lambda_{max}$=260 nm ($\epsilon$=15,000 at pH 7).
FAB-MS (Na salts in glycerol):
Negative mode
m/z=208 (8%: Base–H)$^-$
m/z=418 (32%: M–H)$^-$
m/z=440 (6%: M–2H+Na)$^-$
Positive mode
m/z=210 (1%: Base+H)$^+$
m/z=442 (5%: M+H+Na)$^+$

EXAMPLE 6

Immobilization of $R_P$-/$S_P$-8-AEA-cGMPS to CNBr Agarose 2.9 g CNBr-activated freeze-dried agarose (Pharmacia) are suspended in 1 mM HCl. After swelling the gel is washed with 600 ml of 1 mM HCl. 55 µmol of $S_P$-8-AEA-cGMPS are dissolved in 15 ml of coupling buffer consisting of 0.2M $NaHCO_3$ and 0.5M NaCl and adjusted to pH 8.3 by adding NaOH. The agarose beads are added and the suspension is shaken. High pressure liquid chromatography is used to monitor the decrease of the cyclic nucleotide (RP-18, 4% methanol, 10 mM triethyl ammonium formate buffer). After 24 hours the gel is washed, desactivated with ethanolamine and washed again according to the instructions of the agarose manufacturer. The success of the coupling reaction can be chekked by UV spectroscopy at 260 nm in a suspension of the coupled gel in glycol.

Coupling of the corresponding diastereomer $R_P$-8-AEA-cGMPS is performed likewise.

EXAMPLE 7

Purification of cGMP-dependent Protein Kinases Type II (cGK II) with 8-AEA-cGMPS-Agarose SF 9 cells (approx. $2 \times 10^{-7}$ cells) are harvested 44–48 h after infection with recombinat baculovirus (MOI=10), washed with PBS and suspended in 1 ml buffer (10 mM PIPES, pH 6.8/250 mM ammonium sulphate/2 mM EDTA/ 0.5% Triton X - 100/50 mM benzamidine/50 U/ml trasylol/ 0.7 µg/ml leupeptin/0.5 µg/ml pepstatin A). Lysis of cells is performed by repeated treatment (20×) with a 27 gauge needle syringe. Success is monitored by a microscope. Subsequently the suspension is zentrifuged for 1 hour at 4° C. at 100,000 g. To the supernatant cytosol containing cGK II among other proteins RP-8-AEA-cGMPS agarose (200 µl of settled gel) is added for batch adsorption. Subsequently, the gel is transferred to a zentrifuge column and washed (3×) with buffer (30 mM TRIS, pH 7.4/15 mM mercaptoethanol/ 50 mM benzamidine/1 mM IBMX/2 mM EDTA/300 mM PMSF/600 mM NaCl). Desorption of cGK II is performed by elution with 30 mM cAMP, first at 4° C. and subsequently at room temperature.

Major difficulties in affinity chromatography of cyclic nucleotide-dependent kinases is to get sufficient specific affinity for cGMP-binding proteins but on the other hand to be still able to desorb the protein again under mild conditions which will not destroy natural activity. In case of cGK II it is, in addition, highly desirable to circumvent elution with the natural effector cGMP which, due to its high affinity, would disturb at subsequent binding studies. CAMP is much more convenient here and sufficiently elutes cGK II from the column since the phosphorothioate ligand has lower affinity towards cGMP receptors.

Surprisingly, cGMP phosporothioates are useful as affinity ligands since they have reduced but sufficient affinity to cGMP binding proteins and therefor allow mild elution conditions.

EXAMPLE 8

Cyclic β-phenyl-1,$N^2$-etheno-2'-n-butyryl guanosine-3',5'-monophosphorothioate, $R_P$-diastereomer ($R_P$-PETB-cGMPS)

200 mg (433 µmol) of $R_P$-PET-cGMPS (free acid), are suspended in 5 ml of dry pyridine and 150 ml of butyric acid anhydride added as well as catalytic amounts of dimethylamino-pyridine.

The mixture is refluxed until the starting nucleotide can no longer be detected by reversed phase high pressure liquid chromatography (RP-18, 50% methanol, 100 mM triethyl ammonium formate buffer). The mixture is evaporated and repeatedly evaporated with methanol until pyridine and excess anhydride have been completely removed. The raw product is purified on reversed phase RP-8 silica using 65% methanol and 25 mM phosphate buffer.

The product containing fractions are evaporated to dryness and the residue is extracted with methanol. Evaporation of the filtrate yields 377 µmol (87%) of the butyrylated product.

Formula: $C_{22}H_{22}O_7N_5SP$ (MW 531.5 (free acid)

UV: ($H_2O$): $\lambda_{max}$=252 nm ($\epsilon$=37,400 at pH 7).

What is claimed is:
1. A cyclic guanosine-3',5'-monophosphorothioate of the formula I

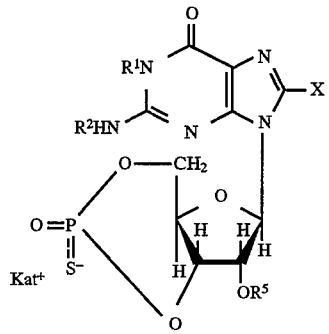

wherein $R^1$ and $R^2$ are hydrogen, $X^1$ is —$CF_3$ or a —$NR^3R^4$ or —$SR^4$ group, wherein $R^3$ is hydrogen and $R^4$ is an alkyl group with a terminal $NH_2$ or OH group, or $R^4$ is a phenyl group having in the 4-position a substituent Y of the formula:

wherein Y is —F, —Cl, —Br, —I, —OH, —SH, —$NH_2$, —$NO_2$, —$OCH_3$, —$CH_3$ or —$CF_3$, or $R^3$ and $R^4$ both are alkyl groups which are connected to each other to form a ring, provided X is not a thiobenzyl group, $R^5$ is hydrogen, a (tri)alkylsilyl group or an acyl group, and Kat$^+$ is a proton or another physiologically acceptable metal cation or a trialkylammonium ion, or $R^1$ and $R^2$ together are a styrylene group and form a condensed tricyclic ring system according to formula II:

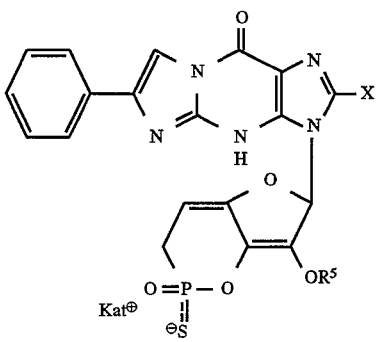

wherein $X^2$ is hydrogen, —F, —Cl, —Br, —I, —$CF_3$ or an —$NR^3R^4$, —$SR^4$ group, wherein $R^3$ is hydrogen and $R^4$ is an alkyl group with a terminal $NH_2$ or OH group, $R^5$ is hydrogen, a (tri)alkylsilyl or an acyl group, and Kat$^+$ is a proton or another physiologically acceptable metal cation or a trialkylammonium ion.

2. A compound according to claim 1 with the equatorial position of the sulfur modification at the thiophosphate moiety ($R_P$-isomer).

3. A compound according to claim 1 with the axial position of the sulfur modification at the thiophosphate moiety ($S_P$-isomer).

4. A compound according to claim 1 wherein $X^1$ is a 4-chlorophenylthio group.

5. A compound according to claim 1 wherein $X^1$ is a 4-hydroxyphenylthio group.

6. A compound according to claim 1 wherein Kat$^+$ is Na$^+$, K$^+$, Li$^+$, ½ Ca$^{2+}$ or ½ Mg$^{2+}$.

7. A compound according to claim 1 wherein $R^3$ and $R^4$ together form a cyclic pentamethylene group.

8. A compound according to claim 1 wherein $R^1$ and $R^2$ together are a styrylene group and $X^2$ is hydrogen.

9. A compound according to claim 1 wherein $R^1$ and $R^2$ together are a styrylene group and $X^2$ is bromine.

10. A compound according to claim 1 wherein $R^5$ is a trialkylsilyl or an acyl group.

11. A compound according to claim 1 wherein $R^5$ is a trimethylsilyl group.

12. A compound according to claim 1 wherein $R^5$ is an acyl group derived from a linear or branched $C_1$-$C_8$ carboxylic acid.

13. A compound according to claim 12 wherein $R^5$ is an n-butyryl group.

14. A compound according to claim 1 wherein in the formulas I and II, $X^1$ or $X^2$ is a molecular spacer having a terminal functional group and is selected from the group consisting of —NHR$^4$ or —SR$^4$, wherein R$^4$ is an alkyl group having a terminal —$NH_2$ or —OH group.

15. A compound according to claim 14 wherein the chain length of the alkyl spacer is 1 to 12 atoms.

16. A compound according to claim 14 wherein $X^1$ or $X^2$ is a 2-aminoethylamino group.

17. A compound according to claim 14 wherein $X^1$ or $X^2$ is a 2-aminoethylthio group.

* * * * *